(12) United States Patent
Harvey

(10) Patent No.: US 9,371,258 B1
(45) Date of Patent: Jun. 21, 2016

(54) HIGH DENSITY FUELS FROM ISOPRENE

(71) Applicant: The United States of America as Represented by the Secretary of the Navy, Washington, DC (US)

(72) Inventor: Benjamin G. Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 212 days.

(21) Appl. No.: 14/314,829

(22) Filed: Jun. 25, 2014

Related U.S. Application Data

(60) Provisional application No. 61/840,019, filed on Jun. 27, 2013.

(51) Int. Cl.
| | |
|---|---|
| *C07C 2/24* | (2006.01) |
| *C07C 2/26* | (2006.01) |
| *C07C 5/03* | (2006.01) |
| *C10L 1/16* | (2006.01) |
| *C07C 5/32* | (2006.01) |
| *C07C 2/42* | (2006.01) |
| *C07C 2/52* | (2006.01) |
| *C10L 1/04* | (2006.01) |
| *C07C 5/02* | (2006.01) |

(52) U.S. Cl.
CPC . *C07C 5/321* (2013.01); *C07C 2/42* (2013.01); *C07C 2/52* (2013.01); *C07C 5/02* (2013.01); *C10L 1/04* (2013.01); *C07C 2523/42* (2013.01); *C07C 2523/44* (2013.01); *C07C 2523/86* (2013.01); *C07C 2525/02* (2013.01); *C07C 2529/70* (2013.01); *C07C 2531/14* (2013.01)

(58) Field of Classification Search
CPC .............. C07C 2/24; C07C 2/26; C07C 5/03; C10L 1/16
USPC ......... 585/255, 511, 512, 521, 522, 523, 524, 585/254; 208/15, 17
See application file for complete search history.

(56) References Cited

PUBLICATIONS

Dzhemilev, et al. Production of regular, linear isoprene oligomers in the presence of Ni-containing homogeneous catalysts, 1979 542. 97:547.315.2.

Audiso, et al. Cationic oligomerization of isoprene and structure of its oligomers. Makromol. Chem, Macromol. Symp. 47, 263-270 (1991).

*Primary Examiner* — Thuan D Dang
(74) *Attorney, Agent, or Firm* — Charlene A. Haley

(57) ABSTRACT

A method for producing high density fuels from isoprene which can be produced via biosynthetic routes using biomass sugars as feedstock. This allows for the production of isoprene and isoprene-derived fuels from abundant waste materials with the potential to significantly reduce DoD carbon emissions. Embodiments of the invention describe a method for conversion of isoprene to full performance jet and diesel fuels. Isoprene can be selectively oligomerized to generate a distribution of branched chain hydrocarbons. Combination of an oligomerization catalyst with a metathesis catalyst allows for the synthesis of high density cyclic fuels with performance advantages (increased density and volumetric net heat of combustion) over conventional petroleum-based fuels.

10 Claims, 1 Drawing Sheet

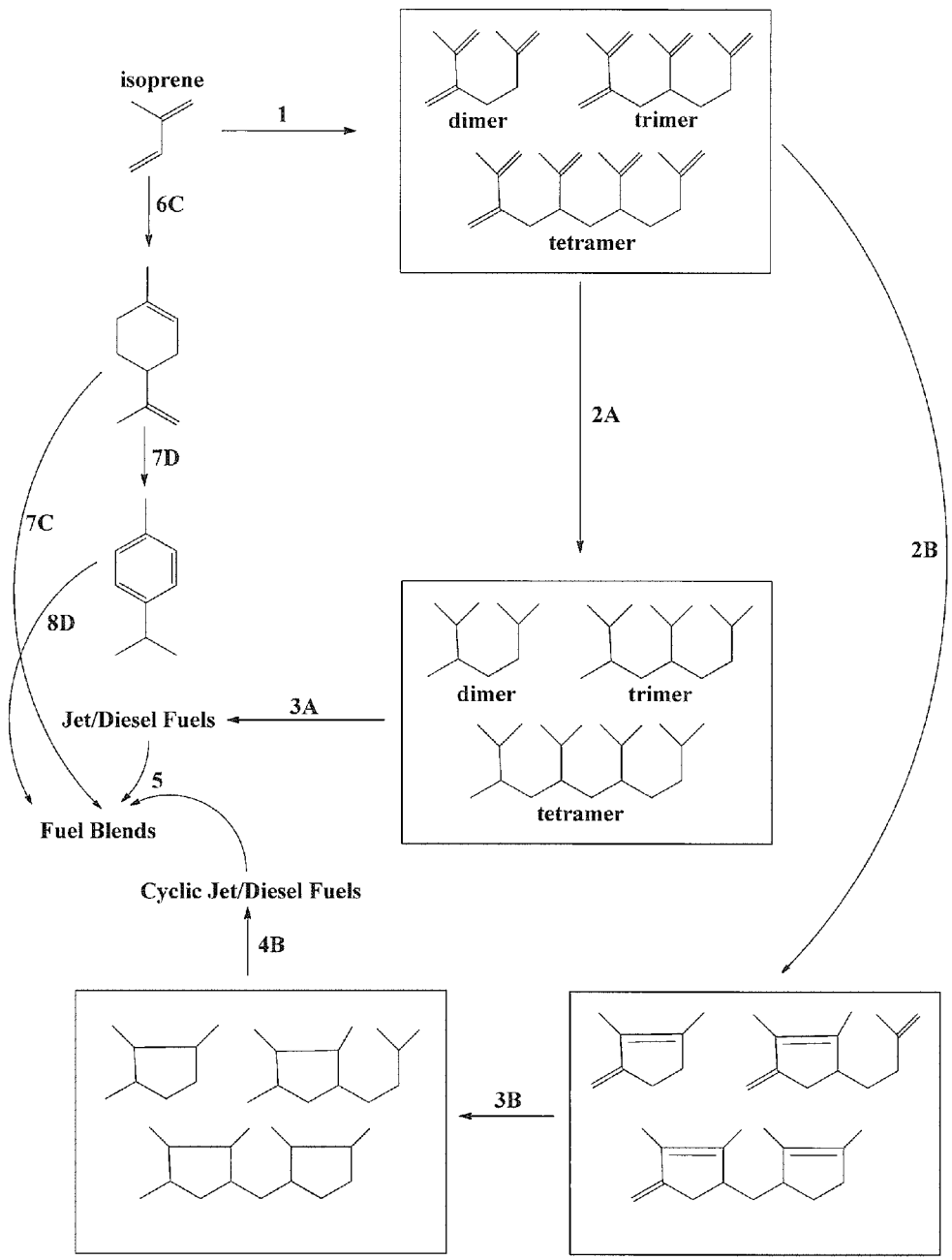

HIGH DENSITY FUELS FROM ISOPRENE

CROSS-REFERENCE TO RELATED APPLICATIONS

This is a non-provisional patent application, claiming the benefit of, parent application Ser. No. 61/840,019 filed on Jun. 27, 2013, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods of making high density fuels from isoprene, and more specifically, isoprene can undergo a Diels-Alder cycloaddition reaction to generate dipentene.

BRIEF DESCRIPTION OF THE DRAWING

FIG. 1 is a flow chart showing how high density fuels are generated from isoprene, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to methods of making high density fuels from isoprene, and more specifically, blends of branched chain, cyclic and aromatic hydrocarbons generated from isoprene.

High density fuels have the potential to improve the range, loiter time, and payload of a variety of Navy systems including jets, missiles, and UAVs. Derivation of these fuels from bio-derived isoprene will reduce Navy/DoD dependence on petroleum-based fuels and will lead to reduced net carbon emissions. Embodiments of the invention describe a selective process for the conversion of isoprene to high density fuels. A range of hydrocarbons with both cyclic and linear structures are generated to produce a full-performance fuel that can be tailored to either jet or diesel engines. Isoprene is generated by a variety of plants and global emissions of this hydrocarbon are estimated at more than 650 million tons per year. Isoprene can also be produced via biosynthetic routes using biomass sugars including lignocellulosic feedstocks. This allows for the production of isoprene and isoprene-derived fuels from abundant waste materials with the potential to significantly reduce DoD carbon emissions. Embodiments of the invention describe a method for conversion of isoprene to full performance jet and diesel fuels. A solvent can be used to dissolve the Ziegler-Natta catalyst and control the reaction rate. Alternatively, isoprene can act as both the reactant and solvent.

Isoprene can be selectively oligomerized to generate a distribution of branched chain hydrocarbons. Combination of an oligomerization catalyst with a metathesis catalyst allows for the synthesis of high density cyclic fuels with performance advantages (increased density and volumetric net heat of combustion) over conventional petroleum-based fuels. Complementary to this process, isoprene can undergo a Diels-Alder cycloaddition reaction to generate dipentene. Blending of linear isoprene oligomers, cyclic oligomers, and dehydrogenated oligomers including p-cymene allows for exquisite control of fuel properties and will allow for the formulation of full-performance renewable jet and diesel fuels.

The following are papers describing oligomerization of isoprene and other 1,3-dienes. The selective trimerization of isoprene with chromium N,N-bis(diarylphosphino)amine catalysts is described in: Bowen, L. E.; Charernsuk, M.; Wass, D. F. Chem. Commun. 2007, 2835-2837. For a review of catalytic oligomerization of 1,3-dienes, see Baker, R. Chem. Rev. 1973, 73, 487. Cationic oligomerization of isoprene is described in: Audisio, G.; Priola, A.; Rossini, A. Makromolekulare Chemie. Macromolecular Symposia 1991, 47, 263-270. The synthesis of linear isoprene oligomers with nickel-containing homogenous catalysts is described in: Dzhemilev, U. M.; Latypov, G. M.; Tolstikov, G. A.; Vostrikova, O. S. Russian Chemical Bulletin 1979, 28, 509-512.

Embodiments of the invention include the following: (please see FIG. 1)

1. Isoprene is allowed to react with a metallocene-based Ziegler Natta catalyst.

2A. The resulting oligomer mixture is hydrogenated to yield a saturated hydrocarbon mixture.

3A. The saturated hydrocarbon mixture is fractionally distilled to generate a fuel, or 2B. The resulting oligomer mixture is allowed to react with a metathesis catalyst to yield cyclic structures.

3B. The cyclic oligomers are hydrogenated to yield a saturated hydrocarbon mixture.

4B. The mixture is fractionally distilled to generate a fuel.

5. Fuels prepared in step 3a and 4b can be blended to generate a fuel mixture, or 6C. Isoprene is converted to cyclic dimers by known methods.

7C. The resulting dimers are hydrogenated and blended with fuels prepared in steps 3a, 4b, or 5, or 7D. Cyclic dimers prepared in step 6C are dehydrogenated to aromatic compounds.

8D. Aromatic compounds prepared in 7D are blended with fuels prepared in 3a, 4b, 5, or 6C.

Further embodiments of the invention include the following: (please see FIG. 1)

1. Isoprene is allowed to react with a metallocene-type catalyst based on metals including, but not limited to, titanium, zirconium, hafnium, or vanadium in the presence of a co-catalyst typically comprised of an aluminum alkyl compound or partially hydrolyzed aluminum alkyl (e.g. methylaluminoxane). The reaction can be carried out with or without a solvent at temperatures in the range of about −20 to about 120 degrees Celsius. In embodiments, the Al/metallocene ratio can be altered to achieve a desired distribution of oligomers. Al/metallocene ratios between 1 and about 1000 are employed.

2A. The resulting oligomer mixture can be directly hydrogenated under a hydrogen atmosphere with a heterogeneous catalyst based on metals that include, but are not limited to, Ni, Pd, Pt, Ru, or Cu. Pressures between 0.1 and about 100 atmospheres and temperatures between ambient and about 250 degrees C. are suitable for this conversion.

3A. The resulting hydrocarbon mixture is purified by fractional distillation to yield a fuel product with the required properties including, but not limited to, flash point, density, and volumetric net heat of combustion.

2B. The resulting oligomer mixture from Step 1 is allowed to react with a metathesis catalyst based on metals including Ru, Mo, W, Re, or Ti. This results in ring closing metathesis (RCM) reactions to yield cyclic oligomers as shown in the supporting information.

3B. The cyclic oligomers are hydrogenated as described in Step 2A.

4B. The hydrogenated cyclic oligomers are purified by fractional distillation as described in Step 3A.

5. In embodiments, fuels produced in Step 3A are blended with fuels produced in Step 4B.

6C. Isoprene is converted to cyclic dimers by Diels Alder cycloaddition. This can be accomplished by addition of heat and/or a catalyst and is promoted by conducting the reaction under pressure.

7C. Cyclic dimers are hydrogenated as described in Step 2A and then are combined with fuel mixtures prepared in Steps 3A, 4B, or 5.

7D. Cyclic dimers prepared in 6C are dehydrogenated to aromatic compounds by methods known in the art.

8D. Aromatic compounds prepared in Step 7D are combined with fuel mixtures prepared in Steps 3a, 4B, 5, or 7C.

Embodiments of the invention generally relate to methods for converting isoprene into fuels including, reacting isoprene with at least one Ziegler-Natta type catalyst based on first metal(s) in the presence of at least one co-catalyst to produce an oligomer mixture of dimers, trimers, and tetramers, hydrogenating the oligomer mixture under a hydrogen atmosphere with at least one heterogeneous catalyst based on second metal(s) at pressures between about 0.1 atmosphere and about 100 atmosphere and at temperatures ranging from about ambient to about 250° C. to produce a substantially or completely saturated hydrocarbon mixture of dimers, trimers, and tetramers, and purifying the hydrocarbon mixture by removing the heterogeneous catalyst to produce substantially or completely saturated fuels.

Another aspect of the invention generally relates to methods for converting isoprene into fuels including, reacting isoprene with at least one metallocene type catalyst based on first metal(s) in the presence of at least one co-catalyst to produce an oligomer mixture of dimers, trimers, and tetramers, reacting the oligomer mixture with at least one metathesis catalyst based on second metal(s) or to produce cyclic oligomers, hydrogenating the oligomer mixture under a hydrogen atmosphere with at least one heterogeneous catalyst based on third metal(s) at pressures between about 0.1 atmosphere and about 100 atmosphere and at temperatures ranging from about ambient to about 250° C. to produce a substantially or purely saturated cyclic hydrocarbon mixture, and purifying the hydrocarbon mixture by removing the heterogeneous catalyst to produce substantially or purely saturated cyclic fuels.

Yet another aspect of the invention generally relates to methods for converting isoprene into fuels including, converting isoprene by a Diels Alder cycloaddition reaction either thermally or with at least one Lewis acid catalyst at temperatures ranging from about −20° C. to about 350° C. and pressures ranging from about 1 atm to 200 atm to produce cyclic dimers, hydrogenating the cyclic dimers under a hydrogen atmosphere with at least one heterogeneous catalyst based on first metal(s) at pressures between about 0.1 atmosphere and about 100 atmosphere and at temperatures ranging from about ambient to about 250° C. to produce a substantially or purely saturated cyclic hydrocarbon mixture and purifying the cyclic hydrocarbon mixture, or alternatively, dehydrogenating the cyclic dimers with at least one heterogeneous dehydrogenation catalyst under an inert or hydrogen atmosphere to generate a mixture of aromatic compounds, unsaturated cyclic hydrocarbons, and cyclic hydrocarbons, and purifying the mixture to produce a pure hydrocarbon mixture.

Embodiments further include at least one solvent to dissolve the Ziegler-Natta catalyst. In embodiments, the Ziegler-Natta type catalyst includes a metallocene catalyst. In embodiments, the removing the heterogeneous catalyst is by fractional distillation. In other embodiments, the Ziegler-Natta type catalyst is a heterogeneous supported catalyst. In embodiments, the first metal(s) is selected from the group consisting of, but not limited to, titanium, zirconium, hafnium, vanadium, chromium, nickel, iron, palladium, platinum, and any combination thereof. In other embodiments, the first metal(s) is selected from the group consisting of titanium, zirconium, hafnium, vanadium, and any combination thereof.

In embodiments, the co-catalyst(s) is selected from the group consisting of, but not limited to, aluminum alkyls, partially hydrolyzed aluminum alkyls (including methylaluminoxane), aromatic borane-based anions, and any combination thereof. In embodiments, the heterogeneous hydrogenation catalyst is selected from the group consisting of, but not limited to, palladium on activated carbon, palladium on charcoal, $PtO_2$, Raney nickel, copper chromite, and any combination thereof. In embodiments, the second metal(s) is selected from the group consisting of, but not limited to, Ni, Pd, Pt, Ru, Cu, and any combination thereof. In embodiments, the reacting isoprene with at least one Ziegler-Natta type catalyst is based on the first metal(s) in the presence of at least one the co-catalyst is at temperatures ranging from about −20° C. to about 120° C. In embodiments, the second metal(s) is selected from the group consisting of, but not limited to, Ru, Mo, Re, Ti, and any combination thereof. In embodiments, the Lewis acid catalyst(s) is selected from the group consisting of, but not limited to, both homogenous and heterogeneous Lewis acids based on Ti, V, Cr, Mn, Fe, Co, Ni, Cu, Zn, Al, B, Sn, and any combination thereof. In embodiments, the cyclic dimers include dipentene(s). In embodiments, the dehydrogenation catalyst is selected from the group consisting of, but not limited to, supported and unsupported Lewis acids, metals including Pt, Pd, Ni, Cu, Zn, Ag, Ir, Rh, Re, Ru, compounds based on these and other suitable metals, and any combination thereof.

In embodiments, the aromatic compound(s) includes p-cymene. In embodiments, the jet and diesel fuel blends in combinations are produced by the methods herein. In embodiments, the fuel blends combinations are produced by the methods herein having greater than or equal to 8% aromatic compounds.

Prophetic examples are for illustration purposes only and not to be used to limit any of the embodiments. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for converting isoprene into fuels, comprising:
   reacting isoprene with at least one Ziegler-Natta type catalyst based on first metal(s) in the presence of at least one co-catalyst to produce an oligomer mixture of dimers, trimers, and tetramers;
   hydrogenating said oligomer mixture under a hydrogen atmosphere with at least one heterogeneous catalyst based on second metal(s) at pressures between about 0.1 atmosphere and about 100 atmosphere and at temperatures ranging from about ambient to about 250° C. to produce a substantially or completely saturated hydrocarbon mixture of dimers, trimers, and tetramers; and
   purifying said hydrocarbon mixture by removing said heterogeneous catalyst to produce substantially or completely saturated fuels.

2. The method according to claim 1, further comprising at least one solvent to dissolve said Ziegler-Natta catalyst.

3. The method according to claim 1, wherein said Ziegler-Natta type catalyst includes a metallocene catalyst.

4. The method according to claim 1, wherein said removing said heterogeneous catalyst is by fractional distillation.

5. The method according to claim 1, wherein said Ziegler-Natta type catalyst is a heterogeneous supported catalyst.

6. The method according to claim 1, wherein said first metal(s) is selected from the group consisting of titanium, zirconium, hafnium, vanadium, chromium, nickel, iron, palladium, platinum, and any combination thereof.

7. The method according to claim 1, wherein said co-catalyst(s) is selected from the group consisting of aluminum alkyls, partially hydrolyzed aluminum alkyls (including methylaluminoxane), aromatic borane-based anions, and any combination thereof.

8. The method according to claim 1, wherein said heterogeneous hydrogenation catalyst is selected from the group consisting of palladium on activated carbon, palladium on charcoal, $PtO_2$, Raney nickel, copper chromite, and any combination thereof.

9. The method according to claim 1, wherein said second metal(s) is selected from the group consisting of Ni, Pd, Pt, Ru, Cu, and any combination thereof.

10. The method according to claim 1, wherein said reacting isoprene with at least one said Ziegler-Natta type catalyst based on said first metal(s) in the presence of at least one said co-catalyst is at temperatures ranging from about −20° C. to about 120° C.

* * * * *